(12) United States Patent
Parikh et al.

(10) Patent No.: US 10,894,125 B2
(45) Date of Patent: Jan. 19, 2021

(54) INFUSION DEVICES AND RELATED RESCUE DETECTION METHODS

(71) Applicant: MEDTRONIC MINIMED, INC., Northridge, CA (US)

(72) Inventors: Neha J. Parikh, West Hills, CA (US); Anirban Roy, Calabasas, CA (US); Benyamin Grosman, Valley Village, CA (US); Rebecca K. Gottlieb, Culver City, CA (US); Di Wu, Montrose, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 148 days.

(21) Appl. No.: 16/162,277

(22) Filed: Oct. 16, 2018

(65) Prior Publication Data
US 2019/0091402 A1 Mar. 28, 2019

Related U.S. Application Data

(63) Continuation of application No. 15/096,156, filed on Apr. 11, 2016, now Pat. No. 10,117,992.
(Continued)

(51) Int. Cl.
*A61M 5/00* (2006.01)
*A61M 5/172* (2006.01)
(Continued)

(52) U.S. Cl.
CPC ...... *A61M 5/1723* (2013.01); *A61M 5/14244* (2013.01); *A61M 5/14248* (2013.01); *A61M 5/168* (2013.01); *A61M 5/172* (2013.01); *A61M 2205/502* (2013.01); *A61M 2205/52* (2013.01); *A61M 2230/005* (2013.01); *A61M 2230/201* (2013.01)

(58) Field of Classification Search
CPC ............ A61M 5/1723; A61M 5/14244; A61M 5/168; A61M 5/172; A61M 5/14248; A61M 2230/005; A61M 2205/52; A61M 2230/201; A61M 2205/502
See application file for complete search history.

(56) References Cited

U.S. PATENT DOCUMENTS

| 4,562,751 A | 1/1986 | Nason et al. |
| 4,685,903 A | 8/1987 | Cable et al. |

(Continued)

*Primary Examiner* — Amber R Stiles
(74) *Attorney, Agent, or Firm* — Shumaker & Sieffert, P.A.

(57) ABSTRACT

Infusion systems, infusion devices, and related operating methods are provided. An exemplary method of operating an infusion device to deliver fluid to a body of a user involves obtaining measurement values for a physiological condition influenced by the fluid, autonomously operating the infusion device to deliver the fluid based at least in part on the measurement values, and detecting a nonactionable condition based on the measurement values. In response to detecting the nonactionable condition, delivery of the fluid is limited while maintaining autonomous operation of the infusion device. In one exemplary embodiment, the nonactionable condition is a rescue condition indicative of the user having consumed fast-acting carbohydrates, and thus insulin delivery may be automatically limited in response to detecting the rescue carbohydrate consumption.

16 Claims, 8 Drawing Sheets

Related U.S. Application Data

(60) Provisional application No. 62/234,471, filed on Sep. 29, 2015.

(51) Int. Cl.
*A61M 5/168* (2006.01)
*A61M 5/142* (2006.01)

(56) References Cited

U.S. PATENT DOCUMENTS

| | | | |
|---|---|---|---|
| 4,755,173 A | 7/1988 | Konopka et al. | |
| 5,080,653 A | 1/1992 | Voss et al. | |
| 5,097,122 A | 3/1992 | Colman et al. | |
| 5,391,250 A | 2/1995 | Cheney, II et al. | |
| 5,485,408 A | 1/1996 | Blomquist | |
| 5,505,709 A | 4/1996 | Funderburk et al. | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,088,608 A | 7/2000 | Schulman et al. | |
| 6,119,028 A | 9/2000 | Schulman et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,485,465 B2 | 11/2002 | Moberg et al. | |
| 6,544,212 B2 | 4/2003 | Galley et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,589,229 B1 | 7/2003 | Connelly et al. | |
| 6,591,876 B2 | 7/2003 | Safabash | |
| 6,641,533 B2 | 11/2003 | Causey, III et al. | |
| 6,659,980 B2 | 12/2003 | Moberg et al. | |
| 6,736,797 B1 | 5/2004 | Larsen et al. | |
| 6,740,072 B2 | 5/2004 | Starkweather et al. | |
| 6,749,587 B2 | 6/2004 | Flaherty | |
| 6,752,787 B1 | 6/2004 | Causey, III et al. | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,817,990 B2 | 11/2004 | Yap et al. | |
| 6,827,702 B2 | 12/2004 | Lebel et al. | |
| 6,932,584 B2 | 8/2005 | Gray et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,323,142 B2 | 1/2008 | Pendo et al. | |
| 7,399,277 B2 | 7/2008 | Saidara et al. | |
| 7,402,153 B2 | 7/2008 | Steil et al. | |
| 7,442,186 B2 | 10/2008 | Blomquist | |
| 7,602,310 B2 | 10/2009 | Mann et al. | |
| 7,621,893 B2 | 11/2009 | Moberg et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,474,332 B2 | 7/2013 | Bente, IV | |
| 8,674,288 B2 | 3/2014 | Hanson et al. | |
| 2003/0060753 A1* | 3/2003 | Starkweather | G06F 19/3468 604/66 |
| 2006/0276771 A1* | 12/2006 | Galley | A61M 5/172 604/503 |
| 2007/0123819 A1 | 5/2007 | Mernoe et al. | |
| 2010/0160861 A1 | 6/2010 | Causey, III et al. | |
| 2014/0066886 A1 | 3/2014 | Roy et al. | |
| 2015/0165117 A1 | 6/2015 | Palerm et al. | |
| 2015/0165119 A1 | 6/2015 | Palerm et al. | |
| 2015/0217051 A1 | 8/2015 | Mastrototaro et al. | |
| 2015/0328402 A1 | 11/2015 | Nogueira et al. | |

\* cited by examiner

INFUSION DEVICES AND RELATED RESCUE DETECTION METHODS

CROSS-REFERENCE TO RELATED APPLICATION(S)

This application is a continuation of U.S. patent application Ser. No. 15/096,156, filed on Apr. 11, 2016, which claims the benefit of U.S. provisional patent application Ser. No. 62/234,471, filed Sep. 29, 2015, the entire content of which is incorporated by reference herein.

TECHNICAL FIELD

Embodiments of the subject matter described herein relate generally to medical devices, and more particularly, embodiments of the subject matter relate to providing rescue detection and related delivery protections during operation of a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner. Regulating blood glucose level is complicated by variations in the response time for the type of insulin being used along with variations in a user's individual insulin response and daily activities (e.g., exercise, carbohydrate consumption, bolus administration, and the like). To compensate for these variations, the amount of insulin being infused in an automated manner may also vary. Reliance solely on currently sensed glucose values may result in delivery adjustments that are too late to avoid a hypoglycemic or hyperglycemic event, so accordingly, predictive algorithms may be utilized to provide estimations of the future blood glucose levels as an aid in regulating the blood glucose level.

One scenario that can be problematic occurs when a user consumes fast-acting carbohydrates, for example, to avoid a potential hypoglycemic event. This, in turn, can result in a spike in the user's blood glucose level, which, in turn, can result in a rising trend in glucose values indicating a need to deliver insulin to mitigate the rise in blood glucose level, thereby unintentionally counteracting the fast-acting carbohydrates. While a quick response time is desired to facilitate a stable blood glucose level, automatically recovering from responding too quickly may not be feasible since infusion devices are generally incapable of undoing a previous delivery. Thus, there is a need to distinguish actionable events that the infusion device should respond to from those that do not require an immediate response.

BRIEF SUMMARY

Infusion systems, infusion devices, and related operating methods are provided. An embodiment of a method of operating an infusion device to deliver fluid capable of influencing a physiological condition to a body of a user is provided. The method involves autonomously operating the infusion device to deliver the fluid based at least in part on measurement values for the physiological condition in the body of the user, detecting a nonactionable condition, such as a rescue condition, based on one or more of the measurement values, and in response to detecting the nonactionable condition, limiting delivery of the fluid while autonomously operating the infusion device.

An embodiment of an infusion system is also provided. The infusion system comprises a sensing arrangement to obtain measurement values for a physiological condition from a body of a user and an infusion device including an actuation arrangement operable to deliver fluid to the body of the user and a control system coupled to the actuation arrangement. The fluid influences the physiological condition of the user, and the control system is configured to autonomously operate the actuation arrangement to deliver a variable rate of infusion based on the measurement values, detect a rescue condition based on one or more of the measurement values, and temporarily limit the variable rate of infusion in response to the rescue condition.

An apparatus of an infusion device is also provided. The infusion device comprises an actuation arrangement operable to deliver fluid to a body of a user, a data storage element to maintain control parameters for a closed-loop operating mode, a communications interface to receive measurement values indicative of a physiological condition in the body of the user influenced by the fluid, and a control module coupled to the actuation arrangement, the data storage element, and the communications interface. The control module is configured to autonomously operate the actuation arrangement to deliver a variable rate of infusion based on the measurement values and the control parameters in accordance with the closed-loop operating mode, detect a rescue condition based on one or more of the measurement values, and temporarily limit the variable rate of infusion in response to the rescue condition.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
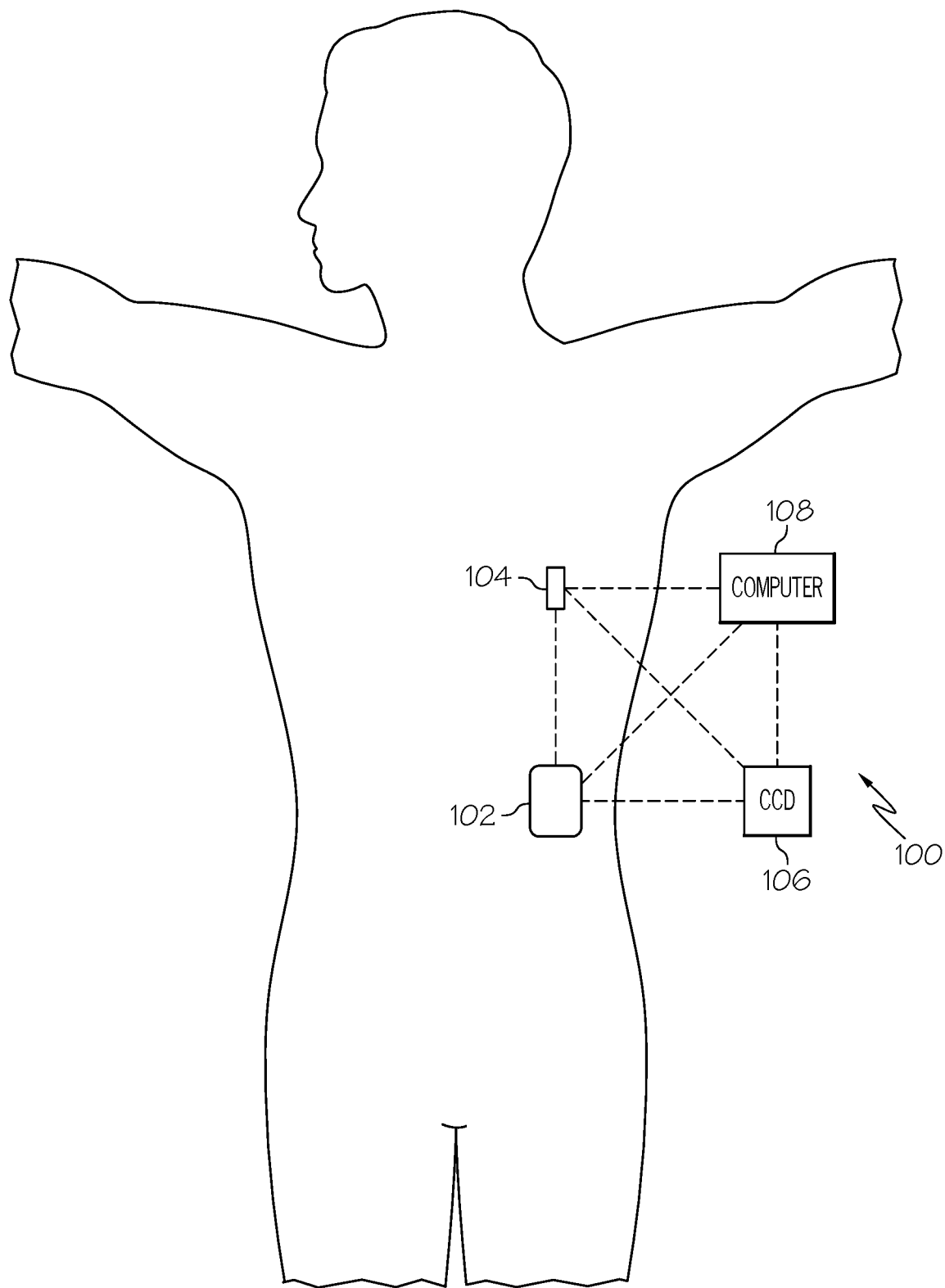
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

As described in greater detail below, primarily in the context of FIG. 8, in exemplary embodiments described herein, a nonactionable condition is detected based on the measurement values for a physiological condition in the body of the user while autonomously operating the infusion device, and in response to detecting the nonactionable condition, the autonomous delivery of the fluid influencing the physiological condition is limited, restricted, or otherwise constrained temporarily, thereby mitigating any potential response to the nonactionable condition. For purposes of explanation, the subject matter is described herein in the context of the nonactionable condition as being a rescue condition where the user has consumed, ingested, or otherwise administered carbohydrates configured to increase his or her blood glucose level and mitigate a potential hypoglycemic event (e.g., fast-acting or "rescue" carbohydrates). In this regard, the rescue condition is detected based on a characteristic of the user's glucose measurement values, such as, for example, a rate of change in the glucose measurement values over successive samples, which occurs at the same time as or after the user's glucose measurement values indicate the potential for a rescue condition exists (e.g., when the user's predicted and/or measured glucose values are low or otherwise indicate a potential hypoglycemic event exists). In essence, a characteristic signature for a rescue condition is detected or otherwise identified from the glucose measurement values. Thereafter, the rate of insulin infusion may be capped or otherwise reduced to limit any potential response to the rescue condition, so that any consumed rescue carbohydrates can achieve their intended effect of avoiding a hypoglycemic condition without undue interference by the autonomous control scheme.

Infusion System Overview

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological or physiological condition of the user, such as a blood glucose level, or the like, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In various embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In one or more exemplary embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
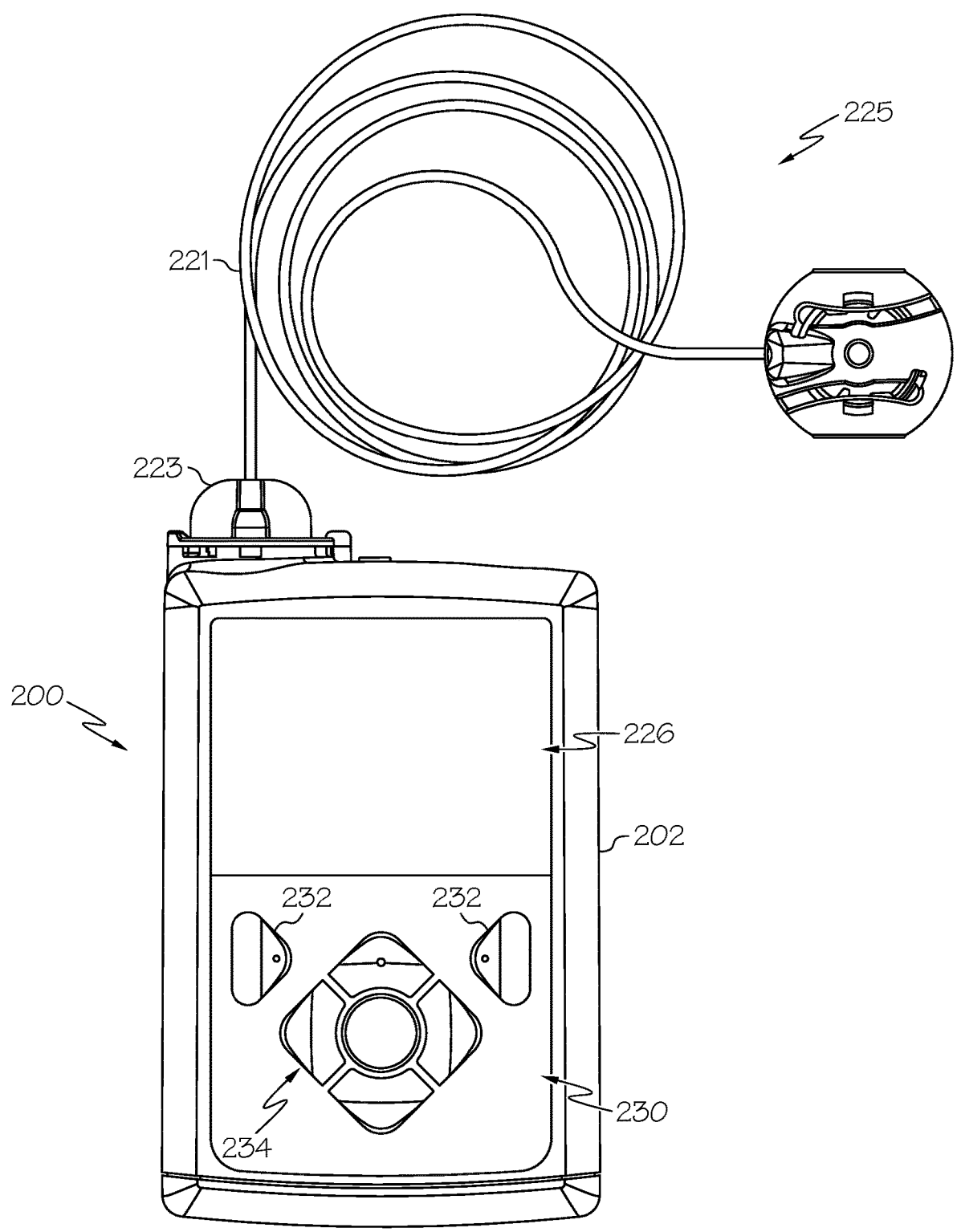
FIG. 2 depicts a plan view of an exemplary embodiment of a fluid infusion device suitable for use in the infusion system of FIG. 1.
Figure 3:
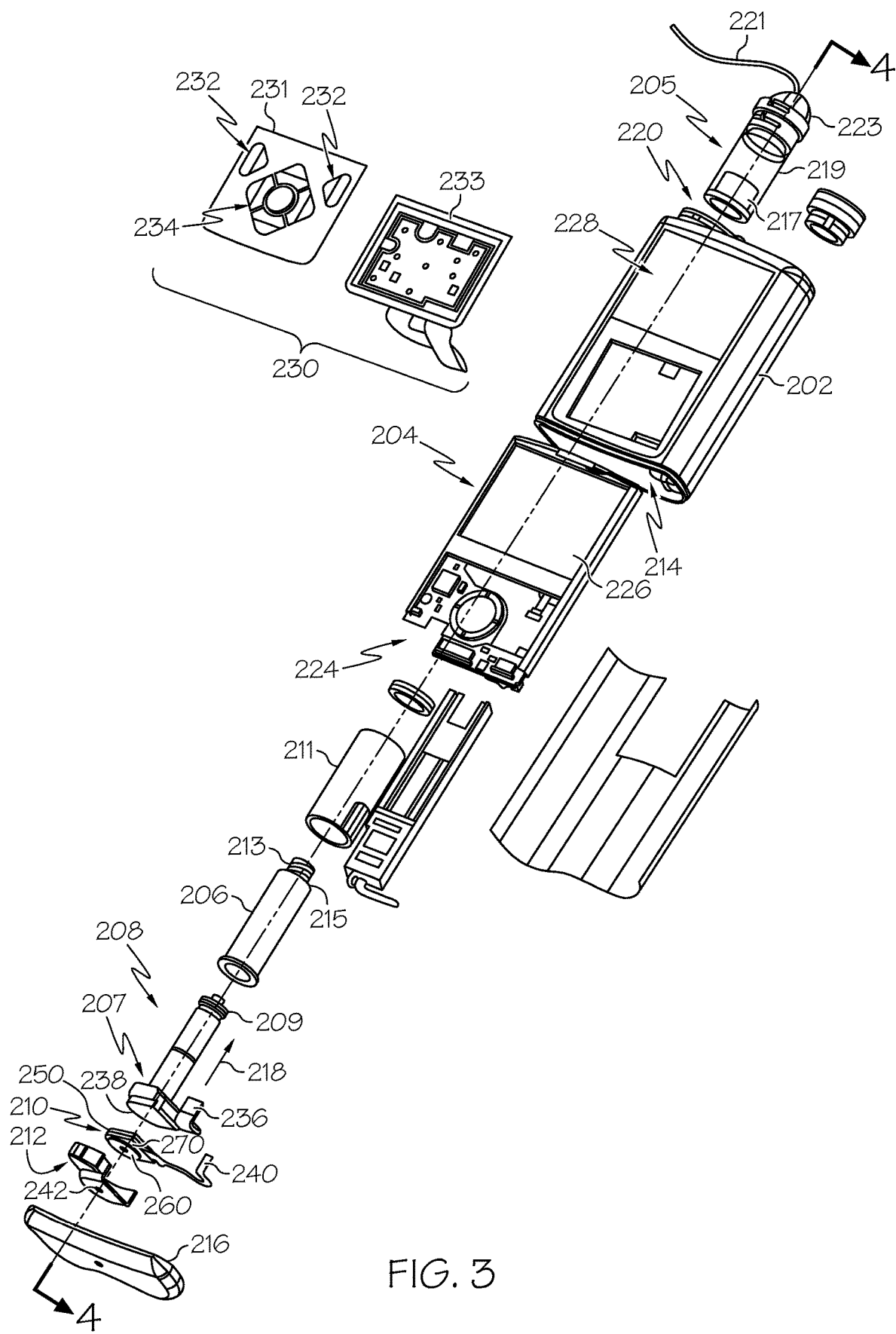
FIG. 3 is an exploded perspective view of the fluid infusion device of FIG. 2.
Figure 4:
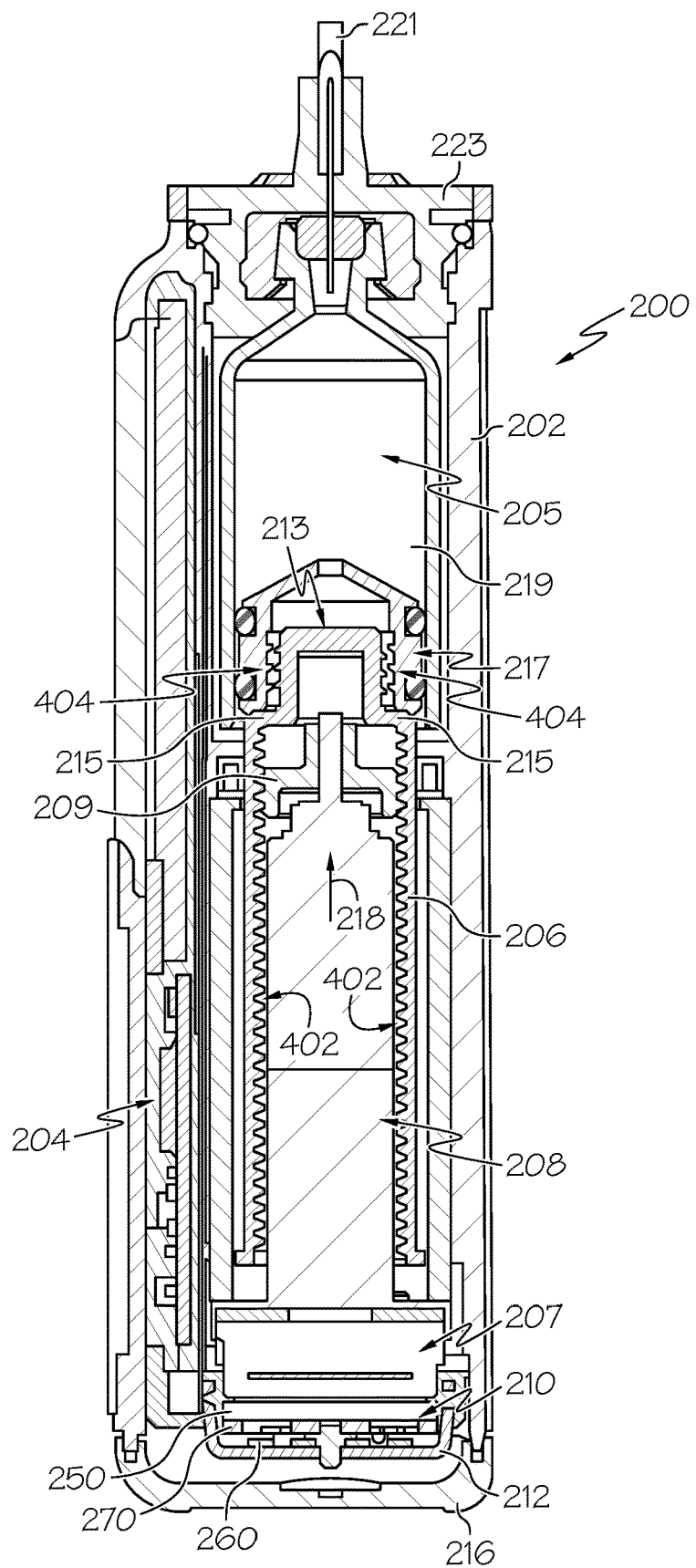
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
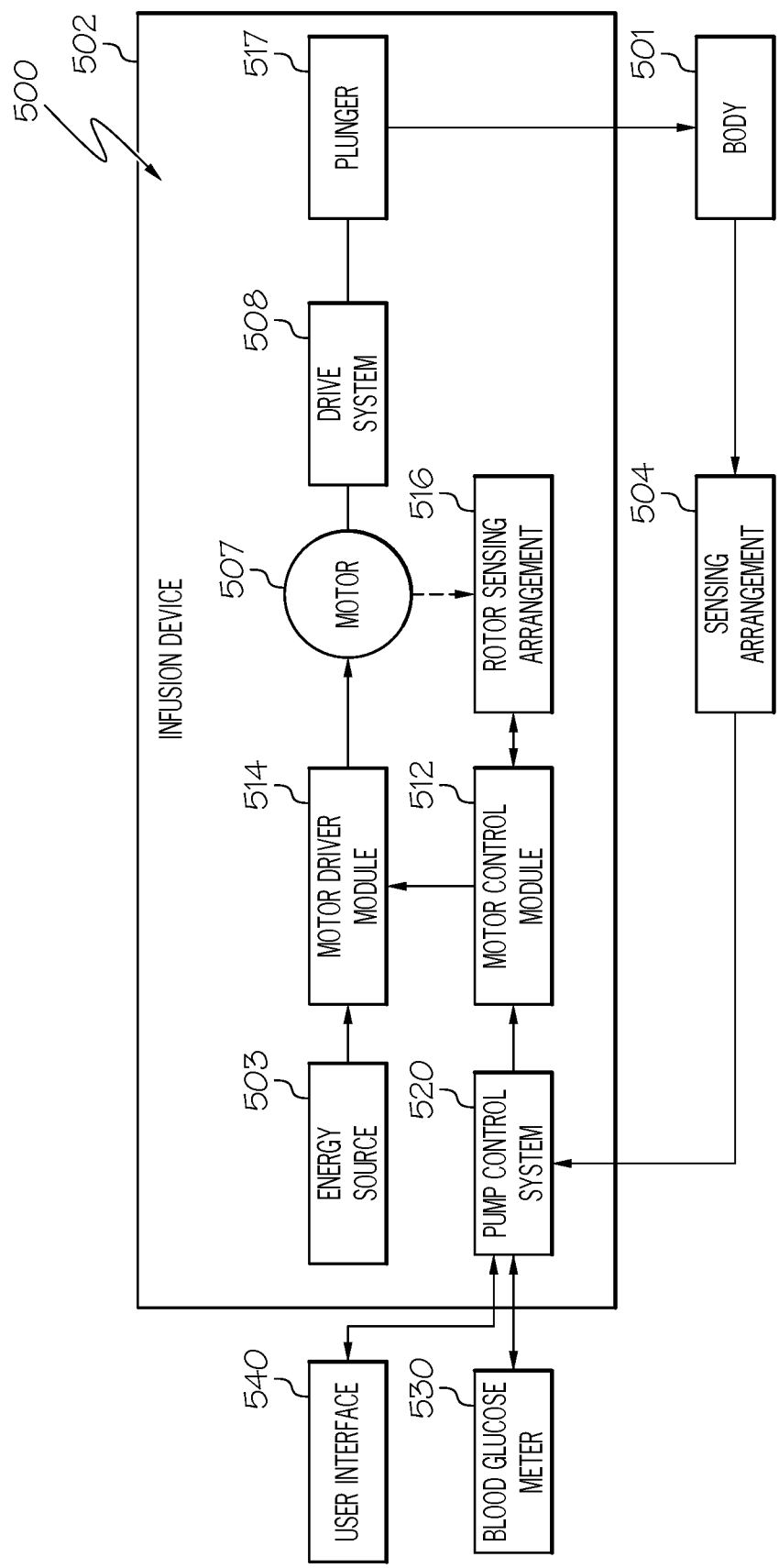
FIG. 5 is a block diagram of an exemplary control system suitable for use in a fluid infusion device, such as the fluid infusion device of FIG. 1 or FIG. 2.

FIG. 5 depicts an exemplary embodiment of a control system 500 suitable for use with an infusion device 502, such as the infusion device 102 in FIG. 1 or the infusion device 200 of FIG. 2. The control system 500 is capable of controlling or otherwise regulating a physiological condition in the body 501 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

In exemplary embodiments, the sensing arrangement 504 includes one or more interstitial glucose sensing elements that generate or otherwise output electrical signals having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In the illustrated embodiment, the pump control system 520 generally represents the electronics and other components of the infusion device 502 that control operation of the fluid infusion device 502 according to a desired infusion delivery program in a manner that is influenced by the sensed glucose value indicative of a current glucose level in the body 501 of the user. For example, to support a closed-loop operating mode, the pump control system 520 maintains, receives, or otherwise obtains a target or commanded glucose value, and automatically generates or otherwise determines dosage commands for operating an actuation arrangement, such as a motor 507, to displace the plunger 517 and deliver insulin to the body 501 of the user based on the difference between a sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit(s), and/or other glucose threshold value(s) in a data storage element accessible to the pump control system 520.

The target glucose value and other threshold glucose values may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 200, 400, while in alternative embodiments, the pump control system 520 may be implemented by a remote computing device that is physically distinct and/or separate from the infusion device 502, such as, for example, the CCD 106 or the computing device 108.

Figure 6:
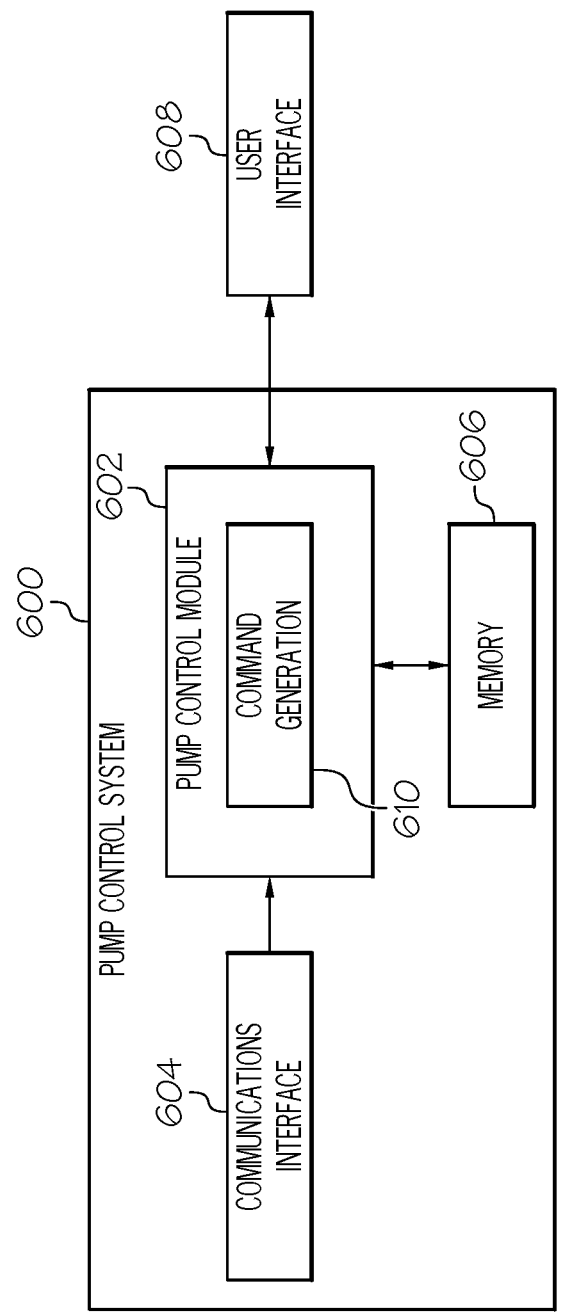
FIG. 6 is a block diagram of an exemplary pump control system suitable for use in the control system of FIG. 5.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In exemplary embodiments, the pump control module 602 is also coupled to one or more user interface elements 608 (e.g., user interface 230, 540) for receiving user input and providing notifications, alerts, or other therapy information to the user. Although FIG. 6 depicts the user interface element 608 as being separate from the pump control system 600, in various alternative embodiments, the user interface element 608 may be integrated with the pump control system 600 (e.g., as part of the infusion device 200, 502), the sensing arrangement 504 or another element of an infusion system 100 (e.g., the computer 108 or CCD 106).

Referring to FIG. 6 and with reference to FIG. 5, the communications interface 604 generally represents the hardware, circuitry, logic, firmware and/or other components of the pump control system 600 that are coupled to the pump control module 602 and configured to support communications between the pump control system 600 and the sensing arrangement 504. In this regard, the communications interface 604 may include or otherwise be coupled to one or more transceiver modules capable of supporting wireless communications between the pump control system 520, 600 and the sensing arrangement 504 or another electronic device 106, 108 in an infusion system 100. In other embodiments, the communications interface 604 may be configured to support wired communications to/from the sensing arrangement 504.

The pump control module 602 generally represents the hardware, circuitry, logic, firmware and/or other component of the pump control system 600 that is coupled to the communications interface 604 and configured to determine dosage commands for operating the motor 506 to deliver fluid to the body 501 based on data received from the sensing arrangement 504 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 506 of the infusion device 502 in an autonomous operating mode based at least in part on a current measurement value for a condition in the body 501 of the user. For example, in a closed-loop operating mode, the command generation application 610 may determine a dosage command for operating the motor 506 to deliver insulin to the body 501 of the user based at least in part on the current glucose measurement value most recently received from the sensing arrangement 504 to regulate the user's blood glucose level to a target reference glucose value. Additionally, the command generation application 610 may generate dosage commands for boluses that are manually-initiated or otherwise instructed by a user via a user interface element 608. For example, regardless of the operating mode being implemented, the command generation application 610 may determine a dosage command for operating the motor 506 to deliver a bolus of insulin to the body 501 of the user that corresponds to a correction bolus or meal bolus amount selected or otherwise indicated by the user via the user interface element 230, 540, 608.

Still referring to FIG. 6, depending on the embodiment, the pump control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the command generation application 610 and perform the tasks, operations, functions, and processes described in greater detail below.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502.

Figure 7:
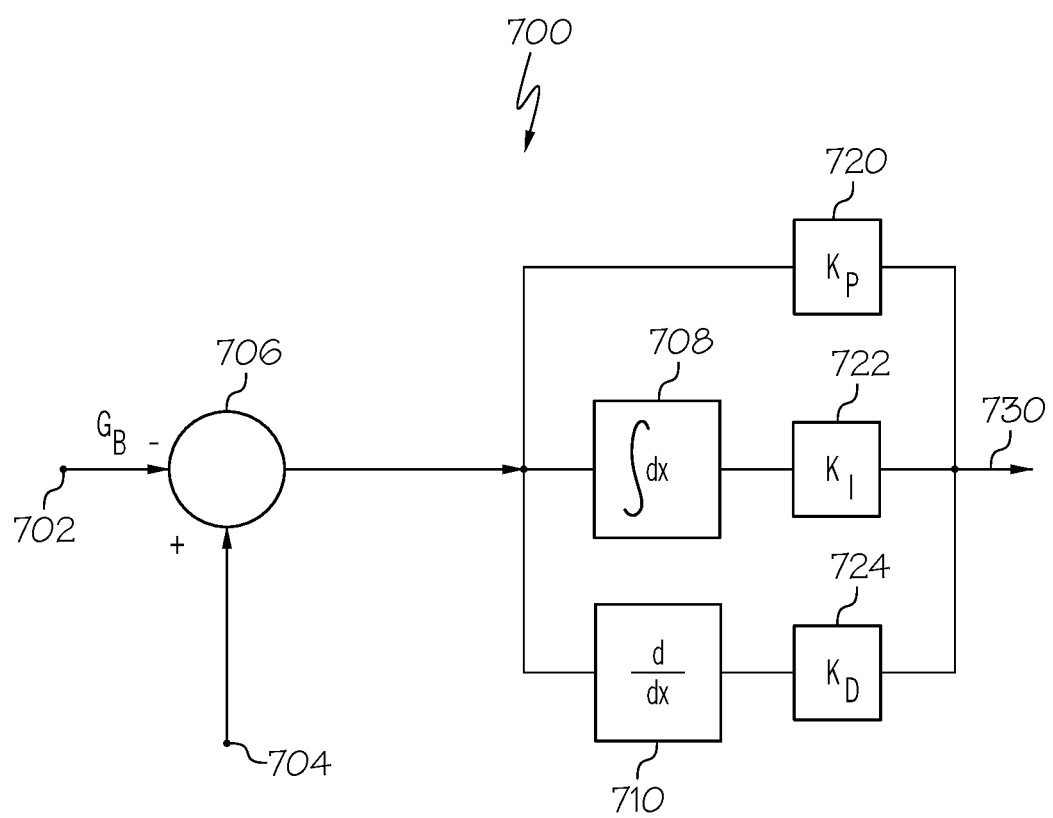
FIG. 7 is a block diagram of a closed-loop control system that may be implemented or otherwise supported by the pump control system in the fluid infusion device of FIG. 5 in one or more exemplary embodiments.

FIG. 7 depicts an exemplary closed-loop control system 700 that may be implemented by a pump control system 520, 600 to provide a closed-loop operating mode that autonomously regulates a condition in the body of a user to a reference (or target) value. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be dynamically calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value (e.g., the most recently obtained sensor glucose value) from the sensing arrangement 504 at input 704. The illustrated control system 700 implements or otherwise provides proportional-integral-derivative (PID) control to determine or otherwise generate delivery commands for operating the motor 510 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 510 to deliver insulin to the body of the user to influence the user's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, $K_P$, to obtain the proportional term. The integral term path includes an integration block 708 that integrates the difference and a gain block 722 that multiplies the integrated difference by an integral gain coefficient, $K_I$, to obtain the integral term. The derivative term path includes a derivative block 710 that determines the derivative of the difference and a gain block 724 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 730. Various implementation details pertaining to closed-loop PID control and determine gain coefficients are described in greater detail in U.S. Pat. No. 7,402,153, which is incorporated by reference.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

Rescue Detection

In exemplary embodiments described herein, a pump control system 520, 600 is configured to detect a rescue condition which should be nonactionable in terms of insulin delivery based on the glucose measurement values obtained from the sensing arrangement 504 while autonomously operating the infusion device 502, and in response, automatically caps, limits, or otherwise restricts insulin delivery temporarily, thereby limiting the response or action that would otherwise be taken by the infusion device 502 autonomously in response to the rescue condition. Thus, when a user consumes fast-acting (or "rescue") carbohydrates to avoid a potential hypoglycemic event while the infusion device is in a closed-loop operating mode, the pump control system 520, 600 recognizes a change in one or more characteristic(s) of the glucose measurement values indicative of a rescue condition and adjusts the autonomous operation of the infusion device in a manner that temporarily reduces insulin delivery. In this regard, once the rescue condition has expired or otherwise elapsed, the pump control system 520, 600 restores the delivery of insulin to the preceding delivery settings. Thus, the pump control system 520, 600 essentially treats a detected rescue condition a nonactionable event and alters the autonomous operation to allow the carbohydrates consumed by the user to achieve their intended effect before resuming normal or preceding regulation of the user's glucose level.

Figure 8:
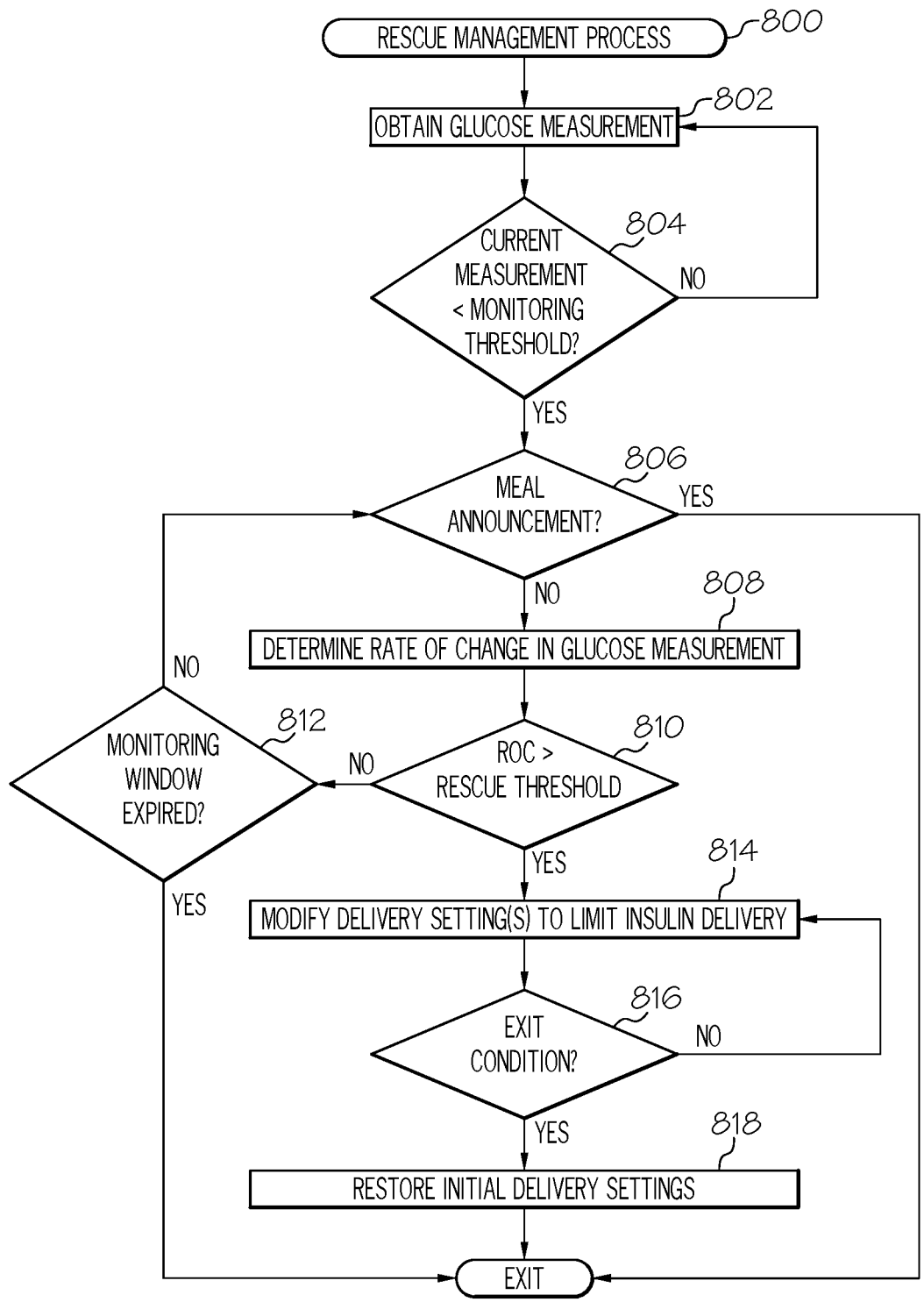
FIG. 8 is a flow diagram of an exemplary rescue management process suitable for use with the control system of FIG. 5 in one or more exemplary embodiments.

FIG. 8 depicts an exemplary rescue management process 800 suitable for implementation by a control system associated with a fluid infusion device, such as a control system 500, 520, 600 in the infusion device 502, to automatically adjust the fluid delivery in a manner that accounts for events that should essentially be nonactionable, such as a rescue condition attributable to a user consuming rescue carbohydrates. For purposes of explanation, the subject matter is described herein in the context of detecting a rescue condition during implementation of a closed-loop operating mode to regulate a user's glucose level; however, it should be appreciated that the subject matter described herein is not necessarily limited to any particular initial operating mode or any particular type of condition being detected.

The various tasks performed in connection with the rescue management process 800 may be performed by hardware, firmware, software executed by processing circuitry, or any combination thereof. For illustrative purposes, the following description refers to elements mentioned above in connection with FIGS. 1-7. In practice, portions of the rescue management process 800 may be performed by different elements of the control system 500, such as, for example, the infusion device 502, the sensing arrangement 504, the pump control system 520, 600, the pump control module 602, and/or the command generation application 610. It should be appreciated that the rescue management process 800 may include any number of additional or alternative tasks, the tasks need not be performed in the illustrated order and/or the tasks may be performed concurrently, and/or the rescue management process 800 may be incorporated into a more comprehensive procedure or process having additional functionality not described in detail herein. Moreover, one or more of the tasks shown and described in the context of FIG. 8 could be omitted from a practical embodiment of the rescue management process 800 as long as the intended overall functionality remains intact.

Referring to FIG. 8 with continued reference to FIGS. 1-7, in exemplary embodiments, the rescue management process 800 is performed while an infusion device is being operated in an autonomous operating mode, such as a closed-loop operating mode. The rescue management process initializes or otherwise begins by obtaining the current (or most recent) glucose measurement from the sensing arrangement and determines whether the current glucose measurement is less than a rescue monitoring threshold (tasks 802, 804). The control system 520, 600 compares the current sensor glucose measurement value from the sensing arrangement 504 (e.g., the value input to the closed-loop control system 700 at input 704) to a monitoring threshold value and detects or otherwise identifies when the current glucose measurement value is less than the monitoring threshold value. In this regard, the rescue monitoring threshold value corresponds to a glucose level below which a user is likely to consume rescue carbohydrates so that the rescue management process 800 does not limit insulin delivery at higher glucose levels where it is unlikely that the user will consume rescue carbohydrates. For example, in one or more embodiments, a threshold value for alerting the user to a potential hypoglycemic event may also be utilized as the rescue monitoring threshold value, or alternatively, the rescue monitoring threshold value may be equal to an alerting threshold value plus an offset value (e.g., to account for a user manually identifying a potential hypoglycemic condition and consuming rescue carbohydrates in advance of an alert). In embodiments where the pump control system 520, 600 is configured to alert a user to consume rescue carbohydrates, the rescue monitoring threshold value may be equal to the threshold value used to generate the rescue carbohydrate alert.

When the rescue management process 800 identifies the current glucose measurement is greater than the rescue monitoring threshold, the autonomous operation of the infusion device is maintained in its current state. For example, in a closed-loop operating mode, the pump control system 520, 600 may autonomously operate the motor 507 of the infusion device 502 to deliver a variable rate of insulin infusion based at least in part on the difference between the current sensor glucose measurement value and a target glucose value configured to regulate the sensor glucose measurement values to the target glucose value, as described above in the context of FIG. 7.

When the rescue management process 800 identifies the current glucose measurement is less than the rescue monitoring threshold, the rescue management process 800 verifies or otherwise confirms that there has not been a meal announcement (task 806). In this regard, when a user manipulates the user interface 540, 608 to initiate a meal bolus or otherwise indicate that a meal is about to be consumed, the rescue management process 800 exits or otherwise terminates, thereby allowing the meal bolus to be delivered unimpeded and with the autonomous operating mode maintaining its current manner of glucose regulation.

In the absence of a meal announcement, the rescue management process 800 monitors or otherwise analyzes subsequent glucose measurements for one or more characteristics indicative of the user having consumed rescue carbohydrates and detects a rescue condition when the characteristic(s) violate a rescue threshold (tasks 808, 810). In exemplary embodiments, for each new glucose measurement value received during a monitoring window after detecting a glucose measurement below the monitoring threshold, the pump control system 520, 600 calculates or otherwise determines a rate of change associated with the respective glucose measurement value and detects a rescue condition when the rate of change associated with the current (or most recent) glucose measurement value exceeds a rescue threshold. For example, the pump control system 520, 600 may calculate the rate of change as the difference between the current sensor glucose measurement and the preceding sensor glucose measurement, where the rescue threshold value represents a change in glucose measurement values over successive samplings indicative of the user having consumed fast-acting rescue carbohydrates. In some embodiments, one or more of the current sensor glucose measurement, the preceding sensor glucose measurement and/or the rate of change associated with the current sensor glucose measurement may be determined by filtering a plurality of preceding glucose measurements. For example, the current sensor glucose measurement most recently received from a sensing arrangement 504 may be updated every 5 minutes, where each current sensor glucose measurement is a filtered average of five preceding output signals sampled at one minute intervals from the sensing element sensitive to a user's glucose level, resulting in a filtered measurement indicative of the user's current glucose level. Some examples of such filtering are described in U.S. patent application Ser. No. 14/281,766, which is incorporated by reference herein in its entirety.

In the absence of glucose measurements indicative of a rescue condition, the rescue management process 800 verifies or otherwise determines whether the rescue monitoring window has elapsed or expired (task 812). In this regard, the pump control system 520, 600 initiates a timer upon detecting a glucose measurement less than a rescue monitoring threshold and ceases monitoring for a rescue condition once the timer value exceeds a value corresponding to a monitoring window duration. The rescue monitoring window duration corresponds to an average duration or time period after consumption during which fast-acting rescue carbohydrates are likely to exhibit an effect on the user's sensor glucose measurement values. For example, the rescue monitoring window duration may be chosen to be 25 minutes or less. In this regard, when the rate of change between any two successive measurement values does not violate the rescue condition detection threshold within the rescue monitoring window, it may be presumed that any carbohydrates consumed were not fast-acting and therefore should be responded to in a normal manner as dictated by the current control scheme or operating mode in effect.

In the illustrated embodiment, the rescue management process 800 terminates or exits when the monitoring window has elapsed, thereby maintaining the normal autonomous operation of the infusion device. However, in other embodiments, the rescue management process 800 may repeat the task of determining whether the current glucose measurement is less than the rescue monitoring threshold after expiration of the monitoring window (task 804), and if so, the rescue management process 800 repeats the loop defined by tasks 806, 808, 810, 812 to detect or otherwise identify a potential rescue condition for as long as the glucose measurements are less than the rescue monitoring threshold upon expiration of a monitoring window. Thus, the rescue management process 800 may continue to monitor for a rescue condition for as long as the current glucose measurement is less than the rescue monitoring threshold until the user's glucose measurements rise above the rescue monitoring threshold to a more normal level.

In response to detecting a rescue condition, the rescue management process 800 automatically modifies or otherwise adjusts one or more delivery settings utilized for autonomously operating the infusion device to limit or otherwise restrict the delivery of fluid for a temporary period of time (tasks 814, 816). For example, in one embodiment, the pump control system 520, 600 modifies or otherwise adjusts the maximum delivery rate or maximum dosage associated with the autonomous operating mode from an initial value to a lower value to temporarily cap the dosage commands generated based on the user's glucose measurement values. In this regard, as a difference between the user's current or predicted glucose measurement value increases in response to the user metabolizing the rescue carbohydrates, the dosage command generated by the pump control system 520, 600 based on that difference in a closed-loop operating mode may be reduced or otherwise constrained to the maximum dosage, regardless of the magnitude of the difference. For example, the maximum delivery rate for the closed-loop operating mode may be temporarily set to a patient-specific safe basal rate of infusion, which may be a fraction of the normal maximum delivery rate for the closed-loop operating mode. In this manner, the response time for the closed-loop control is increased, thereby reducing the autonomous response or action taken in response to the rescue carbohydrates. In another embodiment, the pump control system 520, 600 modifies or otherwise adjusts values for one or more control parameters (e.g., one or more PID gain coefficients 720, 722, 724) to decrease the responsiveness of the autonomous control scheme and thereby limit the dosage or delivery rate that would otherwise be implemented in response to the rise in the user's glucose level.

In one or more embodiments, the pump control system 520, 600 automatically transitions from a closed-loop operating mode to a rescue mode having an associated maximum delivery rate (or maximum dosage) that is less than the maximum delivery rate associated with the closed-loop operating mode. In the rescue mode, the pump control system 520, 600 may continue to generate dosage commands in a manner that is influenced by the current glucose measurement value (or a predicted glucose measurement value based thereon) in a similar manner as is done in the closed-loop operating mode, albeit with the dosage commands being capped or limited to a lower maximum value. In other embodiments, the pump control system 520, 600 may generate dosage commands in a manner similar to the closed-loop operating mode, but with the dosage commands being proportionally scaled down, for example, based on the ratio of the limited maximum delivery rate to the normal closed-loop maximum delivery rate. In yet other embodiments, the rescue mode may correspond to a preexisting safe mode supported by the infusion device 502, in which case the pump control system 520, 600 automatically transitions from a closed-loop operating mode to the safe mode in response to the rescue condition. The safe mode is characterized by a reduced or limited rate of delivery of insulin relative to the normal closed-loop operating mode, for example, by having a lower maximum delivery rate, control parameter coefficients adjusted for a slower response time, or the like.

Still referring to FIG. 8, while autonomously operating the infusion device in a manner that limits delivery, the rescue management process 800 monitors for an exit condition, and in response to detecting an exit condition, the rescue management process 800 automatically restores the infusion delivery to the initial configuration or settings prior to detecting the rescue condition (tasks 816, 818). For example, in one or more embodiments, the pump control system 520, 600 may continually monitor or otherwise analyze glucose and/or predicted glucose measurement values received from the sensing arrangement 504 to detect or otherwise identify an absence of a rescue condition. In this regard, the pump control system 520, 600 may detect characteristics of the glucose measurement values indicative of the rescue carbohydrates being metabolized by the user, such as, for example, when a rate of change between several successive glucose measurement values is less than or equal to zero. In other embodiments, the pump control system 520, 600 identify the absence of the rescue condition when several successive glucose and/or predicted glucose measurement values are greater than a threshold value indicative of the rescue carbohydrates having achieved their intended effect, thereby resuming insulin delivery by the automated closed-loop glucose control system in response to a continuing rise of blood sugar to maintain good glycemic control.

In exemplary embodiments, the pump control system 520, 600 also detects or otherwise identifies an exit condition in response to a meal announcement or other indication of a meal received from the user. Additionally, in one or more embodiments, the pump control system 520, 600 initiates a timer upon entering the rescue mode or otherwise initiating the limited delivery (e.g., task 816) and automatically terminating the rescue mode when the timer value exceeds a maximum threshold duration for the rescue recovery period. Thus, the pump control system 520, 600 ensures the period of limited delivery is only temporary before reverting back to the original delivery configuration for continued regulation of the user's glucose level. In an exemplary embodiment, the maximum threshold duration is a fixed duration of time that the safe (or reduced) delivery rate can be delivered without adversely affecting the glycemic outcome. That said, in other embodiments, the maximum threshold duration may be customizable or patient-specific to reflect varying physiological responses. For example, the maximum threshold duration may be chosen to be equal to a typical postprandial period required for the user's glucose level to peak after consuming rescue carbohydrates, thereby allowing the normal delivery configuration to assist in reducing the user's glucose level if the sensor glucose measurements do not exhibit a postprandial dip. In such embodiments, a patient-specific maximum threshold duration may be determined based on historical measurement data or the like to reflect each user's individual physiology and varying amount of time for reaching a postprandial peak.

It should be noted that any number of exit conditions may be monitored for and/or detected in parallel. For example, the pump control system 520, 600 may continually monitor sensor glucose measurement values and characteristics thereof for indication that the rescue condition is no longer present while also implementing a timeout period and monitoring for any potential meal announcements. By limiting the limited insulin delivery to a temporary duration, rescue carbohydrates may be allowed to achieve their intended effect without risking a potential hyperglycemic event.

After identifying an exit condition, the pump control system 520, 600 automatically restores operation of the infusion device 502 to the initial operating mode and/or the initial delivery settings prior to detecting the rescue condition. For example, the pump control system 520, 600 may restore a maximum delivery rate and/or dosage criteria associated with the closed-loop operating mode. Similarly, if other control parameters for the closed-loop operating mode were adjusted (e.g., PID gain coefficients), the pump control system 520, 600 may restore those control parameters to their initial values. In other embodiments, the pump control system 520, 600 restores the original insulin delivery by automatically transitioning from a rescue mode (or safe mode) back to the original closed-loop operating mode or other autonomous mode preceding the rescue mode. Thus, the pump control system 520, 600 may resume operating the motor 507 in a manner configured to reduce the difference between the current sensor glucose measurement from the sensing arrangement 504 and a target glucose value as described above.

To briefly summarize, the subject matter described herein allows for unannounced rescue carbohydrates consumed by a user to achieve their intended effect unimpeded by the current operating mode in effect when they were consumed by temporarily limiting the delivery of insulin. In this manner, potential hypoglycemic events are more readily avoided by consumption of rescue carbohydrates. At the same time, the period of limited delivery is itself limited, so as to not interfere with long-term regulation of the user's glucose level and provide protection from hyperglycemic events. Accordingly, better overall regulation of the user's glucose level can be achieved without requiring the user to undertake any additional actions upon consuming rescue carbohydrates (i.e., the user does not need to determine the amount of carbohydrates and make a corresponding announcement, manually suspend delivery, or the like).

For the sake of brevity, conventional techniques related to glucose sensing and/or monitoring, closed-loop glucose control, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of operating an infusion device to deliver fluid to a body of a user, the method comprising:
   autonomously operating the infusion device to deliver the fluid based at least in part on measurement values for a physiological condition in the body of the user, the physiological condition being influenced by the fluid delivered by the infusion device;
   after detecting a first measurement value for the physiological condition that violates a first threshold, detecting a rescue condition when a rate of change associated with the measurement values is greater than a second threshold representing a change in the measurement values over successive samplings indicative of the user having consumed rescue carbohydrates, wherein the first threshold comprises a hypoglycemic event alerting threshold value plus an offset value; and
   in response to detecting the rescue condition, limiting delivery of the fluid while autonomously operating the infusion device.

2. The method of claim 1, further comprising:
   detecting an absence of the rescue condition based on one or more of the measurement values after limiting the delivery of the fluid; and
   in response to detecting the absence of the rescue condition, restoring the delivery of the fluid.

3. The method of claim 1, wherein:
   autonomously operating the infusion device comprises autonomously operating the infusion device to deliver a variable rate of infusion based at least in part on the measurement values and a target value for the physiological condition; and
   limiting the delivery of the fluid comprises temporarily capping the variable rate.

4. The method of claim 1, wherein:
autonomously operating the infusion device comprises autonomously operating the infusion device to deliver the fluid in a closed-loop mode based at least in part on the measurement values;
limiting the delivery of the fluid comprises autonomously operating the infusion device to deliver the fluid in a rescue mode; and
a first maximum rate of infusion associated with the rescue mode is less than a second maximum rate of infusion associated with the closed-loop mode.

5. The method of claim 4, further comprising:
detecting an exit condition while autonomously operating the infusion device to deliver the fluid in the rescue mode; and
in response to detecting the exit condition, resuming autonomously operating the infusion device to deliver the fluid in the closed-loop mode.

6. The method of claim 1, further comprising after limiting the delivery of the fluid, restoring the delivery of the fluid in response to a meal indication.

7. The method of claim 1, wherein limiting delivery of the fluid while autonomously operating the infusion device comprises adjusting one or more control parameters of an autonomous control scheme to temporarily decrease responsiveness.

8. The method of claim 1, further comprising determining the rate of change as a difference between successive measurement values.

9. The method of claim 1, wherein the offset value is configured to account for the user consuming the rescue carbohydrates in advance of an alert.

10. An infusion device comprising:
an actuation arrangement operable to deliver fluid to a body of a user;
a data storage element to maintain control parameters for a closed-loop operating mode;
a communications interface to receive measurement values indicative of a physiological condition in the body of the user influenced by the fluid; and
a control module coupled to the actuation arrangement, the data storage element, and the communications interface to autonomously operate the actuation arrangement to deliver a variable rate of infusion based on the measurement values and the control parameters in accordance with the closed-loop operating mode, detect a rescue condition indicative of the user having consumed fast-acting carbohydrates after a first measurement value violates a first threshold when a rate of change associated with one or more of the measurement values is greater than a second threshold representing a change in the measurement values over successive samplings indicative of the user having consumed fast-acting carbohydrates, and temporarily limit the variable rate of infusion in response to the rescue condition, wherein the first threshold comprises a hypoglycemic event alerting threshold value plus an offset value.

11. The infusion device of claim 10, wherein the control module adjusts the one or more of the control parameters to decrease responsiveness of the closed-loop operating mode in response to the rescue condition.

12. The infusion device of claim 10, the control parameters including closed-loop gain coefficients, wherein the control module adjusts the one or more of the closed-loop gain coefficients to temporarily limit the variable rate of infusion in response to the rescue condition.

13. The infusion device of claim 10, the control parameters including a maximum delivery rate, wherein the control module adjusts the maximum delivery rate to a lower delivery rate to temporarily limit the variable rate of infusion in response to the rescue condition.

14. A method of operating an infusion device to deliver fluid to a body of a user, the method comprising:
autonomously operating the infusion device to deliver the fluid in a closed-loop operating mode based at least in part on measurement values for a physiological condition in the body of the user, the physiological condition being influenced by the fluid delivered by the infusion device; and
in response to detecting a rescue condition based on the measurement values, automatically transitioning from the closed-loop operating mode to a rescue mode configured to limit delivery of the fluid while autonomously operating the infusion device, wherein autonomously operating the infusion device in the rescue mode comprises proportionally scaling dosage commands generated in accordance with the closed-loop operating mode based on a ratio of a limited maximum delivery rate associated with the rescue mode to a normal closed-loop maximum delivery rate.

15. The method of claim 14, wherein the rescue mode has a maximum dosage associated therewith that is less than a corresponding maximum dosage associated with the closed-loop operating mode.

16. The method of claim 14, wherein the rescue mode comprises a safe mode having one or more of a lower maximum delivery rate than the closed-loop operating mode or control parameter coefficients adjusted for a slower response time than the closed-loop operating mode.

* * * * *